US005563307A

United States Patent [19]

Schaerfl, Jr. et al.

[11] Patent Number: 5,563,307
[45] Date of Patent: * Oct. 8, 1996

[54] FLUID MIXTURES OF METHYLIDENE- OR METHYL-SUBSTITUTED LINEAR HYDROCARBONS AND DERIVATIVES THEREOF

[75] Inventors: Robert A. Schaerfl, Jr.; Ali M. Dadgar, both of Baton Rouge; Carroll W. Lanier, Baker, all of La.

[73] Assignee: Albemarle Corporation, Richmond, Va.

[*] Notice: The portion of the term of this patent subsequent to Dec. 14, 2013, has been disclaimed.

[21] Appl. No.: 447,290

[22] Filed: May 22, 1995

Related U.S. Application Data

[63] Continuation-in-part of Ser. No. 166,774, Dec. 14, 1993, Pat. No. 5,516,958.

[51] Int. Cl.$^6$ .................................. C10M 107/16
[52] U.S. Cl. ................. 585/12; 585/10; 585/500; 508/110
[58] Field of Search ............................. 585/10, 12, 500

[56] References Cited

U.S. PATENT DOCUMENTS

| | | | |
|---|---|---|---|
| 3,324,191 | 6/1967 | Wofford | 260/669 |
| 3,351,621 | 11/1967 | Bacskai | 260/88.2 |
| 3,356,754 | 12/1967 | Wofford | 260/669 |
| 3,360,580 | 12/1967 | Mertzweiller et al. | 260/669 |
| 3,472,830 | 10/1969 | Baxter et al. | 260/94.2 |
| 3,624,175 | 11/1971 | Zuech | 260/677 R |
| 4,041,088 | 8/1977 | Bach et al. | 260/668 B |
| 4,049,732 | 9/1977 | Bach et al. | 260/668 B |
| 4,060,492 | 11/1977 | Yasui et al. | 252/59 |
| 4,061,780 | 12/1977 | Yoshida et al. | 424/358 |
| 4,078,010 | 3/1978 | Prillieux et al. | 260/676 R |
| 4,340,705 | 7/1982 | Lai et al. | 526/139 |
| 4,440,965 | 4/1984 | Palmer | 585/12 |
| 4,551,503 | 11/1985 | Lai et al. | 525/332.1 |
| 5,306,856 | 4/1994 | Streck et al. | 585/508 |
| 5,366,658 | 11/1994 | Hoppe et al. | 252/56 S |

FOREIGN PATENT DOCUMENTS

| | | | |
|---|---|---|---|
| 779363 | 2/1968 | Canada | 260/691 |
| 0390492 | 10/1990 | European Pat. Off. | C08F 136/20 |
| 0518021 | 12/1992 | European Pat. Off. | C07C 2/30 |

OTHER PUBLICATIONS

Marvel et al, J. Am. Chem. Soc., vol. 81 (1959) pp. 4736–4744.
Chemical Abstracts, vol. 111, 1989, Abstract No. 78655x.
Chemical Abstracts, vol. 104, 1986, Abstract No. 226170h.
Chemical Abstracts, vol. 97, 1982, Abstract No. 164341r.
Chemical Abstracts, vol. 96, 1982, Abstract No. 35923n.
Chemical Abstracts, vol. 79, 1973, Abstract No. 79272c.
Chemical Abstracts, vol. 68, 1968, Abstract No. 3340a.

*Primary Examiner*—Ponnathapura Achutamurthy
*Attorney, Agent, or Firm*—Philip M. Pippenger

[57] ABSTRACT

Novel fluid mixtures of specified hydrocarbons meeting an array of structural criteria are described. Linear hydrocarbons having terminal double bonds and internal segments of specified differing chain lengths separated by one or more carbon atom(s) each of which has a methylidene substituent make up one group of such compounds. Another group is alkenyl end-capped compounds of the first group. Third and fourth groups are products formed by hydrogenation of the first and second groups, respectively. The products, whether end-capped or not, and whether hydrogenated or not, have desirable lubricating properties such as suitably low pour points and/or low NOACK volatility and/or very high viscosity index and thus can be used as base oils or as components in formulating lubricants.

46 Claims, No Drawings

FLUID MIXTURES OF METHYLIDENE- OR METHYL-SUBSTITUTED LINEAR HYDROCARBONS AND DERIVATIVES THEREOF

REFERENCE TO RELATED APPLICATION

This is a continuation-in-part of prior application Ser. No. 08/166,774, filed Dec. 14, 1993, now U.S. Pat. No. 5,516,958.

TECHNICAL FIELD

This invention relates generally to diene oligomers and more specifically to linear $\alpha,\omega$-diene oligomers which have reactive vinylidene groups along the backbone of the oligomer chain and which are useful as lubricants and lubricant additives.

BACKGROUND

Synthetic hydrocarbon lubricants are known in the art. For example, polyalphaolefins (PAO's) are made by oligomerizing $C_6$ to $C_{20}$ $\alpha$-olefins. These oligomer fluids are usually hydrogenated to improve their stability to oxidation. The residual internal double bond in each molecule can also be functionalized to form, for example, alkyl phenols, carboxylic acids and esters, alcohols, mercaptans, aldehydes, sulfonates and the like. However, the hindered nature of the double bond can make functionalization difficult, especially with higher oligomers. Also, because only one double bond is available, the ability to form multifunctional molecules is limited.

U.S. Pat. No. 5,306,856 granted Apr. 26, 1994 to Streck et al. describes a method of manufacturing methylidene-group-containing $\alpha,\omega$-unsaturated oligomers from $\alpha,\omega$-diolefins in the presence of organoaluminum compounds as catalysts. The reaction is performed at 150°–350° C. The products of the reaction are identified by the formula:

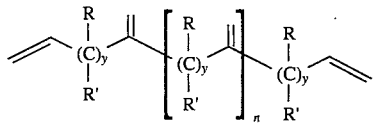

where R and R' each independently represent hydrogen or an alkyl, aryl, aralkyl or cycloalkyl group; x is 1 or a number between 3 and 25; y=x or x+2; n is a number between 1 and 99; and $$\Sigma\, C_k = (x+4)(n+2)-(n+1)$$

is the expression for the sum of the C-atoms in the chain.

THE INVENTION

We have found that substantially straight chain, low molecular weight synthetic fluids can be prepared by oligomerizing $\alpha,\omega$-dienes using an aluminum alkyl catalyst. These oligomers possess a series of vinylidene groups along the backbone of the oligomer chain which are readily available to react so as to permit the easy formation of derivatives of the oligomers.

This invention provides, inter alia, fluid mixtures of specified hydrocarbons meeting an array of structural criteria which, whether end-capped or not, and whether hydrogenated or not, have desirable lubricating properties such as suitably low pour points and/or low NOACK volatility and/or very high viscosity index and thus can be used as base oils or as components in formulating lubricants.

In one embodiment of the invention there is provided a hydrogenated saturated synthetic lubricant which has excellent lubricant properties, including low NOACK volatility and a very high viscosity index, said lubricant consisting essentially of a mixture of hydrocarbons of particular chemical structures described hereinafter.

In accordance with an embodiment of this invention there is provided a process for preparing a substantially linear oligomer of a $\alpha,\omega$-diene which has vinylidene groups along and directly attached to the oligomer chain. The process comprises reacting an $\alpha,\omega$-diene in the presence of an organoaluminum catalyst so as to form said oligomer.

Pursuant to one preferred embodiment of this invention there is provided a novel fluid mixture of vinylidene hydrocarbons having linear backbones and methylidene group(s) depending therefrom, said mixture consisting essentially of hydrocarbons having the formula

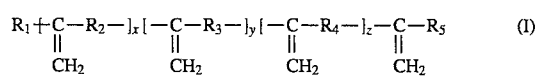

wherein $R_1$ and $R_5$ are omega-alkenyl groups having, independently, n or n+2 carbon atoms, and where n is the minimum number of linear carbon atoms in each said alkenyl group and is at least 6;

$R_2$ is an alkylene group that has a length of n carbon atoms and which may contain one or more hydrocarbyl substituents depending therefrom, but which preferably is an unsubstituted polymethylene group having n carbon atoms;

$R_3$ is an alkylene group that has a length of n+2 carbon atoms and which may contain one or more hydrocarbyl substituents depending therefrom, but which preferably is an unsubstituted polymethylene group having n+2 carbon atoms;

$R_4$ is an alkylene group that has a length of n-2 carbon atoms and which may contain one or more hydrocarbyl substituents depending therefrom, but which preferably is an unsubstituted polymethylene group having n-2 carbon atoms; and x, y, and z are, independently, integers from 0 to about 100.

This mixture is further characterized in that:

a) the groups depicted within brackets in formula (I) are disposed within the individual molecules such that substantially all molecules of formula (I) in which the sum of x, y and z is 3 or more contain at least two different groups depicted within brackets in that formula; and b) this mixture of hydrocarbons has a pour point of −10° C. or below, and a viscosity index of 150 or above.

Those molecules as depicted in formula (I) in which the sum of x, y and z is 3 or more that do not contain at least two different groups depicted within brackets in formula (I) contain the depicted groups containing $R_2$, but do not contain the depicted groups containing $R_3$ or $R_4$.

Another preferred embodiment of this invention provides novel fluid mixtures of end-capped vinylidene hydrocarbons, said mixture consisting essentially of hydrocarbons having the formula:

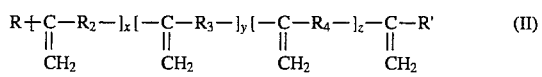

wherein

R and R' are, independently, aliphatic hydrocarbon groups each having from 12 to about 40 carbon atoms and one olefinic double bond, mostly as a methylidene group; and $R_2$, $R_3$, $R_4$, x, y, and z are as defined above with reference to formula (I).

This mixture is further characterized in that:

a) the groups depicted within brackets in formula (II) are disposed within the individual molecules such that substantially all molecules of formula (II) in which the sum of x, y and z is 3 or more contain at least two different groups depicted within brackets in that formula; and b) this mixture of hydrocarbons has a pour point of −10° C. or below, and a viscosity index of 150 or above.

Those molecules as depicted in formula (II) in which the sum of x, y and z is 3 or more that do not contain at least two different groups depicted within brackets in formula (II) contain the depicted groups containing $R_2$, but do not contain the depicted groups containing $R_3$ or $R_4$.

Another feature of the above-described fluid mixtures of vinylidene hydrocarbons of formulas (I) and (II) is that they can contain up to about 2 mol percent (preferably no more than about 1 mol percent) of olefinically unsaturated hydrocarbon molecules in the same molecular weight range as the molecules of formulas (I) and (II) but in which the linear backbone itself contains internal olefinic unsaturation, and for each such internal double bond there is one less dependant methylidene group in the molecule. The amount of such internal double bond-containing molecules in the fluid product mixture is primarily a function of reaction temperature used in producing the mixture. For example, when the product is formed at temperatures in the range of about 120° to about 130° C. the product will typically contain up to about 1 mole percent of such internal double bonded molecules. But at temperatures above about 140° C. the extent of internal double bond formation can increase dramatically. Thus at about 140° C., products having at least 12 mol percent of internal double bonded molecules are typically formed. In situations wherein the product is to be used without prior hydrogenation as a lubricant or lubricant additive for high temperature service in the presence of air, the amount of internal double bond-containing species in the vinylidene hydrocarbon product should be no more than about 2 mol percent, as substantially greater amounts can lead to oxidative instability and possible chain scission.

A further preferred embodiment of this invention comprises a novel fluid mixture of hydrocarbons having linear backbones and methyl group(s) depending therefrom, said mixture consisting essentially of hydrocarbons having the formula

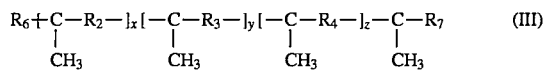

wherein $R_6$ and $R_7$ are alkyl groups having, independently, n or n+2 carbon atoms, and where n is the minimum number of linear carbon atoms in each said alkyl group and is at least 6; and $R_2$, $R_3$, $R_4$, x, y, and z are as defined above with reference to formula (I).

This mixture being further characterized in that:

a) the groups depicted within brackets in formula (III) are disposed within the individual molecules such that substantially all molecules of formula (III) in which the sum of x, y and z is 3 or more contain at least two different groups depicted within brackets in that formula; and b) this mixture of hydrocarbons has a pour point of −10° C. or below, a NOACK volatility of 9 or below, and a viscosity index of 150 or above.

Those molecules as depicted in formula (III) in which the sum of x, y and z is 3 or more that do not contain at least two different groups depicted within brackets in formula (III) contain the depicted groups containing $R_2$, but do not contain the depicted groups containing $R_3$ or $R_4$.

Yet another preferred embodiment of this invention is a novel fluid mixture of hydrocarbons having linear backbones and methyl group(s) depending therefrom, said mixture consisting essentially of hydrocarbons having the formula

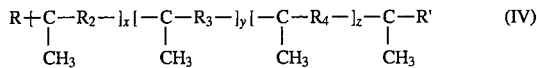

wherein

R and R' are alkyl groups having, independently, 12 to about 40 carbon atoms; and $R_2$, $R_3$, $R_4$, x, y, and z are as defined above with reference to formula (I).

This mixture is further characterized in that:

a) the groups depicted within brackets in formula (IV) are disposed within the individual molecules such that substantially all molecules of formula (IV) in which the sum of x, y and z is 3 or more contain at least two different groups depicted within brackets in that formula; and b) this mixture of hydrocarbons has a pour point of −10° C. or below, and a viscosity index of 150 or above.

Those molecules as depicted in formula (IV) in which the sum of x, y and z is 3 or more that do not contain at least two different groups depicted within brackets in formula (IV) contain the depicted groups containing $R_2$, but do not contain the depicted groups containing $R_3$ or $R_4$.

Another feature of the above-described fluid mixtures of methyl-branched hydrocarbons of formulas (III) and (IV) is that they may contain up to about 2 mol percent of one or more saturated hydrocarbon molecules formed by hydrogenation of the internally unsaturated hydrocarbon molecules referred to above in connection with formulas (I) and (II).

Additional preferred embodiments of this invention are fluid mixtures in accordance with the respective formulas (I), (II), (III) and (IV) above wherein the sum of x, y and z in substantially all molecules of formula (I), (II), (III) or (IV) (as the case may be) is no higher than about 100, more preferably no higher than about 10, and most preferably no higher than about 6.

Non-limiting examples of α,ω-dienes for use in the above process of the invention, are α,ω-dienes containing from 8 to 30 carbon atoms in the chain. They can be substituted elsewhere than at the double bonds by alkyl, cycloalkyl, aryl or aralkyl groups having from 1 to 30 carbon atoms, but preferably are substantially linear, unsubstituted α,ω-dienes. Specific α,ω-dienes include 1,7-octadiene, 1,8-nonadiene, 1,9-decadiene, 1,10-undecadiene, 1,11-dodecadiene, 1,12-tridecadiene, 1,13-tetradecadiene, 1,14-pentadecadiene, 1,15-hexadecadiene, 1,16-heptadecadiene, 1,17-octadecadiene, 1,18-nonadecadiene, 1,19-eicosadiene, and the like including mixtures thereof. By choosing different dienes, the spacing between the vinylidene groups can be selected to provide oligomers whose properties are tailored to specific applications. It is to be noted that when a single α,ω-diene hydrocarbon is used in the oligomerization, n in the above formulas is an integer that is two less than the number of linear carbon atoms in the diene. For example, if 1,7-octadiene is oligomerized, n is 6, whereas in products derived from 1,9-decadiene, n is 8. Products of this type wherein n is in the range of 6 to 18 are preferred.

Suitable aluminum alkyl compounds for use as catalysts preferably contain two or three alkyl groups, each having from 1 to about 20 carbon atoms. Non-limiting examples of aluminum alkyls include trimethylaluminum, triethylaluminum, tri-n-propylaluminum, tri-n-butylaluminum, triisobutylaluminum, tri-n-hexylaluminum, tri-n-octylaluminum, tri-n-decylaluminum, tri-n-dodecylaluminum, diisobutylaluminum hydride, and the like. The catalysts are used in effective amounts to oligomerize the $\alpha,\omega$-diene. Preferably, mole ratios of catalyst to diene of from about 1:1,000 to 1:10 are used with mole ratios of from about 1:20 to 1:100 being preferred.

The reaction can be carried out neat or in the presence of an inert dry organic solvent. Non-limiting examples of suitable solvents or diluents include linear and cyclic aliphatic hydrocarbons containing from about 5 to 20 carbon atoms, such as pentane, isopentane, hexane, cyclohexane, heptane, octane, decane, hexadecane, and the like, and aromatic solvents having from about 6 to 20 carbon atoms such as benzene, toluene, xylene, ethylbenzene, cumene mesitylene, and the like.

The reaction temperatures are chosen to provide oligomerization in a reasonable time without causing side reactions such as isomerization of the vinylidene groups or the formation of excessive amounts (i.e., more than about 2 mol percent) of deep internal olefins and, preferably, range from about 50° to 140° C. More preferably the temperature ranges from 100° to 140° C. and most preferably from 120° to 125° C. As noted above, at temperatures above 140° C. the mechanism of internal olefin formation becomes significant. Temperatures of 120° to 125° C. maximize the formation of the desired vinylidene products (90%+) at reasonable reaction times. Reaction pressures preferably range from atmospheric to about 1,000 psig. The oligomers have number average molecular weights $M_n$ ranging from about 150 to 3,000 and, preferably, from about 250 to 1,800.

"End-capping" of the vinyl groups at the end of the oligomer chain is accomplished by adding $C_6$ to $C_{30}$ alpha mono-olefins to the reaction. A vinylidene is formed at the reaction site but the new ends of the polymer are saturated and unreactive. Under relatively mild conditions, the vinylidene groups along the chain do not react. Some of the added alpha-olefins react with themselves to form vinylidene compounds.

Non-limiting examples of alpha-olefins which can be used for end-capping include 1-butene, 1-pentene, 1-hexene, 1-octene, 1-decene, 1-dodecene, 1-tetradecene, 1-hexadecene, 1-octadecene, and the like including mixtures thereof. Preferably, amounts of from about 0.05 to 5 moles of alpha-olefin per mole of $\alpha,\omega$-diene are used.

The vinylidene hydrocarbon mixtures of formula (I) above, exemplified by oligomerization of 1,9-decadiene, comprise the following dimer, trimers, tetramers and pentamers (as well as higher oligomers): 9-methenyl-1,19-eicosadiene; 9,18-dimethenyl-1,29-triacontadiene; 9,20-dimethenyl-1,29-triacontadiene; 11,18-dimethenyl-1,29-triacontadiene; 9,18,27-trimethenyl-1,39-tetracontanadiene; 9,20,27-trimethenyl-1,39-tetracontanadiene; 9,20,29-trimethenyl-1,39-tetracontanadiene; 11,18,27-trimethenyl-1,39-tetracontanadiene; 9,18,27,36-tetramethenyl-1,49-pentacontanadiene; 9,18,27,38-tetramethenyl-1,49-pentacontanadiene; 9,18,29,36-tetramethenyl-1,49-pentacontanadiene; 9,18,29,38-tetramethenyl-1,49-pentacontanadiene; 9,20,27,36-tetramethenyl-1,49-pentacontanadiene; 9,20,27,38-tetramethenyl-1,49-pentacontanadiene; 9,20,29,36-tetramethenyl-1,49-pentacontanadiene; 11,18,27,36-tetramethenyl-1,49-pentacontanadiene; 11,18,29,36-tetramethenyl-1,49-pentacontanadiene; 11,20,27,36-tetramethenyl-1,49-pentacontanadiene; etc.

Hydrogenation of the above product mixture yields a mixture as depicted in formula (III) above, that includes the following $C_{20}$, $C_{30}$, $C_{40}$, $C_{50}$ (and higher molecular weight) methyl-branched hydrocarbons: 9-methyl-1,19-eicosane; 9,18-dimethyl-1,29-triacontane; 9,20-dimethyl-1,29-triacontane; 11,18-dimethyl-1,29-triacontane; 9,18,27-trimethyl-1,39-tetracontane; 9,20,27-trimethyl-1,39-tetracontane; 9,20,29-trimethyl-1,39-tetracontane; 11,18,27-trimethyl-1,39-tetracontane; 9,18,27,36-tetramethyl-1,49-pentacontane; 9,18,27 38-tetramethyl-1,49-pentacontane; 9,18,29,36-tetramethyl-1,49-pentacontane; 9,18,29,38-tetramethyl-1,49-pentacontane; 9,20,27,36-tetramethyl-1,49-pentacontane; 9,20,27,38-tetramethyl-1,49-pentacontane; 9,20,29,36-tetramethyl-1,49-pentacontane; 11,18,27,36-tetramethyl-1,49-pentacontane; 11,18,29,36-tetramethyl-1,49-pentacontane; 11,20,27,36-tetramethyl-1,49-pentacontane; etc.

The endcapping reaction is illustrated below using 1-dodecene as the alpha-olefin. Mixtures of alpha-olefins can also be used.

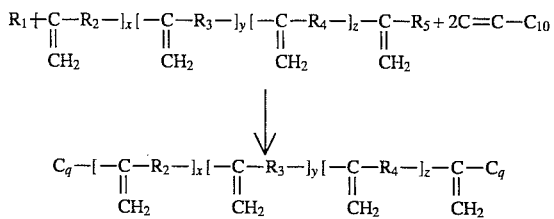

where $R_1$, $R_2$, $R_3$, $R_4$, $R_5$, x, y and z are as defined in connection with formula (I) above, and $C_q$ is a $C_{10}$ or $C_{12}$ hydrocarbyl group.

The oligomers can be hydrogenated by conventional methods. Supported nickel catalysts are especially useful. For example, nickel on a Kieselguhr support gives good results. Batch or continuous processes can be used. For example, the catalyst can be added to the oligomer liquid and stirred under hydrogen pressure or the oligomer liquid can be passed through a fixed bed of the supported catalyst under hydrogen pressure. Hydrogen pressures of about 100 to 1,000 psig at temperatures of about 150° C. to 300° C. are especially useful.

The vinylidene groups along the oligomer chain of the unhydrogenated oligomer can also be reacted to form useful derivatives. For example, the groups can either be coupled with another oligomer molecule, cross-coupled with other olefins, such as vinylidenes, to form branched polyolefins and/or reacted with various compounds such as acrylic acid, maleic anhydride succinic anhydride, phenols, halogen, hydrogen halides, hydrogen sulfide, etc. to add functional groups along the polymer chain. Also, non-end-capped oligomers can be recovered from the oligomerization reaction and the different reactivities of the vinylidene and vinyl groups used to sequentially react the vinylidene group and the vinyl groups with different reagents to form multifunctional compounds or two oligomer molecules can be coupled through the vinylidene group to form tetra-alpha-olefins.

The invention is further illustrated by, but is not intended to be limited to, the following examples.

EXAMPLE 1

A mixture of 99.8 g of 1,7-octadiene and 4.6 g of tri-n-octyl aluminum (TNOA) was prepared. The mixture was then stirred and heated to 115° C., maintained near that temperature for 52 hours, and cooled. The pressure was ambient, and the vapor space was free of air and moisture.

The reaction mass was sampled after 0, 21, 45, and 93 hours from the beginning of the run. At the end of the reaction, 52.0 g of hexane were added to the "gel" as a diluent. Then, 54.6 g of 25% caustic were added to "kill" the TNOA. The aqueous layer was separated from the organic layer in a separatory funnel.

| Time (hours)      | 0     | 21   | 45   | 93   |
|-------------------|-------|------|------|------|
| wt. % octadiene   | 100.0 | 91.2 | 66.6 | 10.4 |
| mol % alpha       | 100.0 | 97.0 | 88.3 | 16.0 |
| mol % vinylidene  | 0.0   | 3.0  | 11.7 | 78.8 |

EXAMPLES 2–7

A series of oligomerizations of 1,9-decadiene were conducted as in Example 1 using tri-n-octylaluminum as the catalyst with the catalyst loadings, reaction times and temperatures listed in Table 1 below. Increasing the temperature greatly enhanced the conversion of monomer. NMR analyses showed that the products are almost exclusively vinylidenes.

TABLE I

|   | Catalyst | Diene | Catalyst: Diene Weight Ratio | Catalyst: Diene Molar Ratio | Temperature (°C.) | Time (Hours) | Conversion (%) | Product Distribution $C_{20}:C_{30}:C_{40}$ |
|---|---|---|---|---|---|---|---|---|
| 2 | tri-n-octyl-aluminum | 1,9-decadiene | 1:10 | 1:27 | 25 | 18 | — | ND[1] |
|   |   |   |   |   | 50 | 70 | — | 1:2:ND |
| 2a | tri-n-octyl-aluminum | 1,9-decadiene | 1:10 | 1:27 | 105 | 24 | — | 2:2:1 |
| 3 | tri-n-octyl-aluminum | 1,9-decadiene | 1:11 | 1:30 | 105 | 19 | — | 10:5:1 |
|   |   |   |   |   | 105 | 42 | — | 5:2:1 |
| 4 | tri-n-octyl-aluminum | 1,9-decadiene | 1:11 | 1:30 | 105 | 19 | 61 | 5:1:ND |
| 5 | tri-n-octyl-aluminum | 1,9-decadiene | 1:11 | 1:30 | 130 | 6 | — | 3:2:1 |
| 6 | tri-n-octyl-aluminum | 1,9-decadiene | 1:11 | 1:30 | 150 | 2 | 52 | 20:7:1 |
|   |   |   |   |   |   | 6 | 85 | 3:3:1 |
| 7 | tri-n-octyl-aluminum | 1,9-decadiene | 1:22 | 1:60 | 105 | 24 | 72 | 4:1:trace |

[1]ND = none detected

EXAMPLE 8

1,9-Decadiene (1122.6 grams) was oligomerized using 95 grams of tri-n-octyl aluminum catalyst. The temperature ranged from about 105° C. to 118° C. and the total reaction time was 64.2 hours. The analysis of the product is shown below.

|              | Wt %  |                 | Mole % |
|--------------|-------|-----------------|--------|
| decadiene    | 40.3  | vinyl           | 74.3   |
| $C_{20}$     | 30.0  | vinylidene      | 23.7   |
| $C_{30}$     | 15.7  | tri-substituted | 0.0    |
| other lights | 0.9   | internal        | 2.0    |
| $C_{40}$     | 7.4   |                 |        |
| $C_{50}$     | 3.4   |                 |        |
| $C_{60}$     | 1.3   |                 |        |
| other heavies| 1.1   |                 |        |

The product was fractionated by distillation and a mostly decadiene trimer ($C_{30}$) fraction was hydrogenated. The synthetic fluid had a very low NOACK volatility and a very high viscosity index. Table II shows its properties compared to a commercial hydrogenated 4 cSt 1-decene PAO.

TABLE II

|        | Visc. (cSt) @ 100° C. | Visc. (cSt) @ 40° C. | Pour Pt. (°C.) | NOACK (wt. %) | VI  |
|--------|-----------------------|----------------------|----------------|---------------|-----|
| Ex. 8  | 3.6                   | 12.3                 | −18            | 7.4           | 195 |
| PAO    | 3.9                   | 16.8                 | <−65           | 13.0          | 129 |

Example 9 illustrates another embodiment of the invention in which the α,ω-diene oligomer is reacted with a molar excess of a vinylidene olefin using a $BF_3$ catalyst which is activated by a proton source such as $H_2O$ or an alcohol. The vinylidene olefin preferably contains from about 8 to 60 carbon atoms and is a dimer of an α-olefin having from about 4 to 30 carbon atoms. More preferably the vinylidene olefin has from about 12 to 40 carbon atoms and is reacted in amounts of from about 0.1 to 20 moles per mole of α,ω-diene oligomer.

EXAMPLE 9

A $C_{20,30}$ decadiene oligomer fraction ($C_{20}$ 1.9 mole, $C_{30}$ 1.0 mole) was reacted with excess (27.5 mole) $C_{16}$ vinylidene ($C_8$ dimer) using a $BF_3$-MeOH catalyst (0.8% $BF_3$ and 0.13 wt. % MeOH). The conversion was 71 wt. after 56 minutes. Of all the remaining material, 99 wt. % was $C_{16}$ tri-substituted olefin. After the unreacted $C_{16}$ and by-product $C_{32,36}$ were distilled away a very linear medium viscosity product resulted. The properties of the unhydrogenated product compared with a 10 cSt 1-decene PAO product are shown in Table III below.

TABLE III

|       | Visc. (cSt) @ 100° C. | Visc. (cSt) @ −40° C. | Pour Pt. (°C.) | VI  |
|-------|-----------------------|------------------------|----------------|-----|
| PAO   | 9.6                   | 32650                  | −53            | 137 |
| Ex. 9 | 11.6                  | 36490                  | −48            | 147 |

EXAMPLE 10

A mixture of 98.1 grams of 1,7-octadiene and 515.2 grams of 1-decene were reacted in the presence of 49.2 grams of tri-n-octyl aluminum catalyst. The temperature ranged from about 113° to 118° C. and the reaction was continued for a total of 144.6 hours. The conversion of diene was 76.7 wt. %. The product distribution was as shown below:

|  | Wt. % |
|---|---|
| Octadiene | 3.3 |
| $C_{10}$ | 28.4 |
| $C_{16}$ | 1.9 |
| $C_{18}$ | 16.3 |
| $C_{20}$ | 30.4 |
| Theoretical |  |
| Other lights | 0.9 |
| $C_{24,26,28}$ | 13.4 |
| $C_{32,34,36}$ | 3.8 |
| Other heavies | 1.1 |

EXAMPLES 11–18

The variety and range of physical properties possessed by unhydrogenated fluid mixtures of vinylidene hydrocarbons of this invention are illustrated by the data in Tables IV and V. The tables identify the diene subjected to oligomerization ("$C_{10}$" is 1,9-decadiene and "$C_8$" is 1,7-octadiene) and where end-capping was used, the 1-olefin employed as the end-capping agent was 1-decene ("$C_{10}$"). In Tables IV and V, "nd" means not determined.

TABLE IV

| Example | 11 | 12 | 13 | 14 |
|---|---|---|---|---|
| Diene | $C_{10}$ | $C_{10}$ | $C_{10}$ | $C_8$ |
| 1-Olefin | none | none | none | none |
| Dimer, wt % | 52.3 | 0.7 | 0 | 4.6 |
| Trimer, wt % | 46.4 | 92.8 | 59.3 | 89.0 |
| Tetramer, wt % | 1.3 | 6.5 | 38.8 | 6.3 |
| Pentamer, wt % | 0 | 0.1 | 1.9 | 0 |
| Visc., cSt @ 100° C. | 2.15 | 3.29 | 4.06 | 2.06 |
| Visc., cSt @ 40° C. | 6.09 | 10.9 | 14.6 | 5.94 |
| Visc., cSt @ −25° C. | nd | nd | nd | 79.4* |
| Pour point, °C. | −36 | −27 | −27 | −51 |
| VI | 187 | 191 | 196 | 165 |

*Viscosity at −40° C. was 225 cSt

TABLE V

| Example | 15 | 16 | 17 | 18 |
|---|---|---|---|---|
| Diene | $C_8$ | $C_8$ | $C_8$ | $C_8$ |
| 1-Olefin | none | none | $C_{10}$ | $C_{10}$ |
| Dimer, wt % | 0.1 | 0.1 | 3.1 | 0 |
| Trimer, wt % | 24.7 | 8.0 | 92.9 | 25.4 |
| Tetramer, wt % | 68.9 | 41.0 | 4.0 | 50.2 |
| Pentamer, wt % | 5.2 | 50.7 | 0 | 24.4 |
| Visc., cSt @ 100° C. | 3.25 | 26.7 | 2.84 | 5.7 |
| Visc., cSt @ 40° C. | 11.2 | 172 | 9.27 | 24.3 |
| Visc., cSt @ −25° C. | nd | nd | nd | nd |
| Pour point, °C. | −42 | −36 | −18 | −27 |
| VI | 172 | 192 | 169 | 189 |

The fluid mixtures of this invention may be produced by other procedures such as by synthesis and blending together of individual compounds or by use of suitable thermal cracking procedures. However, use of low temperature (100° to 130° C. and most preferably 120° to 125° C.) oligomerization of α,ω-dienes is the preferred method presently known.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A fluid mixture of vinylidene hydrocarbons having linear backbones and methylidene group(s) depending therefrom, said mixture consisting essentially of hydrocarbons having the formula

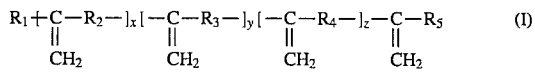

wherein $R_1$ and $R_5$ are omega-alkenyl groups having, independently, n or n+2 carbon atoms, and where n is the minimum number of linear carbon atoms in each said alkenyl group and is at least 6;

$R_2$ is an alkylene group having a length of n carbon atoms;

$R_3$ is an alkylene group having a length of n+2 carbon atoms and n is at least 6;

$R_4$ is an alkylene group having a length of n−2 carbon atoms;

x, y, and z are, independently, integers from 0 to about 100;

said mixture being further characterized in that:

a) the groups depicted within brackets in formula (I) are disposed within the individual molecules such that substantially all molecules of formula (I) in which the sum of x, y and z is 3 or more contain at least two different groups depicted within brackets in formula (I); and b) said fluid mixture of vinylidene hydrocarbons has a pour point of −10° C. or below, and a viscosity index of 150 or above.

2. A fluid mixture in accordance with claim 1 wherein the sum of x, y and z in substantially all molecules of formula (I) is no higher than about 100.

3. A fluid mixture in accordance with claim 1 wherein the sum of x, y and z in substantially all molecules of formula (I) is no higher than about 10.

4. A fluid mixture in accordance with claim 1 wherein the sum of x, y and z in substantially all molecules of formula (I) is no higher than about 6.

5. A fluid mixture in accordance with claim 1 wherein $R_2$ is an unsubstituted polymethylene group having n carbon atoms; $R_3$ is an unsubstituted polymethylene group having n+2 carbon atoms; and $R_4$ is an unsubstituted polymethylene group having n−2 carbon atoms.

6. A fluid mixture in accordance with claim 5 wherein n is 6.

7. A fluid mixture in accordance with claim 5 wherein n is 8.

8. A fluid mixture in accordance with claim 5 wherein n is 6 and wherein the sum of x, y and z in substantially all molecules of formula (I) is no higher than about 10.

9. A fluid mixture in accordance with claim 5 wherein n is 8 and wherein the sum of x, y and z in substantially all molecules of formula (I) is no higher than about 10.

10. A fluid mixture in accordance with claim 1 wherein said mixture has a number average molecular weight of up to about 3,000.

11. A fluid mixture of end-capped vinylidene hydrocarbons having linear backbones and methylidene group(s) depending therefrom, said mixture consisting essentially of hydrocarbons having the formula:

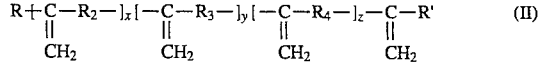

wherein

R and R' are, independently, aliphatic hydrocarbon groups each having from 12 to about 40 carbon atoms and one olefinic double bond therein;

$R_2$ is an alkylene group having a length of n carbon atoms;

$R_3$ is an alkylene group having a length of n+2 carbon atoms;

$R_4$ is an alkylene group having a length of n−2 carbon atoms;

x, y, and z are, independently, integers from 0 to about 100 and n is at least 6;

said mixture being further characterized in that:
- a) the groups depicted within brackets in formula (II) are disposed within the individual molecules such that substantially all molecules of formula (II) in which the sum of x, y and z is 3 or more contain at least two different groups depicted within brackets in formula (II); and
- b) said mixture of end-capped vinylidene hydrocarbons has a pour point of −10° C. or below, and a viscosity index of 150 or above.

12. A fluid mixture in accordance with claim 11 wherein the sum of x, y and z in substantially all molecules of formula (II) is no higher than about 100.

13. A fluid mixture in accordance with claim 11 wherein the sum of x, y and z in substantially all molecules of formula (II) is no higher than about 10.

14. A fluid mixture in accordance with claim 11 wherein the sum of x, y and z in substantially all molecules of formula (II) is no higher than about 6.

15. A fluid mixture in accordance with claim 11 wherein $R_2$ is an unsubstituted polymethylene group having n carbon atoms; $R_3$ is an unsubstituted polymethylene group having n+2 carbon atoms; and $R_4$ is an unsubstituted polymethylene group having n−2 carbon atoms.

16. A fluid mixture in accordance with claim 15 wherein n is 6.

17. A fluid mixture in accordance with claim 15 wherein n is 8.

18. A fluid mixture in accordance with claim 15 wherein n is 6 and wherein the sum of x, y and z in substantially all molecules of formula (I) is no higher than about 10.

19. A fluid mixture in accordance with claim 15 wherein n is 8 and wherein the sum of x, y and z in substantially all molecules of formula (I) is no higher than about 10.

20. A fluid mixture in accordance with claim 11 wherein said mixture has a number average molecular weight of up to about 3,000.

21. A fluid mixture of hydrocarbons having linear backbones and methyl group(s) depending therefrom, said mixture consisting essentially of hydrocarbons having the formula:

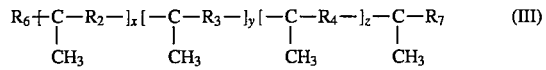

wherein $R_6$ and $R_7$ are alkyl groups having, independently, n or n+2 carbon atoms, and where n is the minimum number of linear carbon atoms in each said alkyl group and is at least 6;

$R_2$ is an alkylene group having a length of n carbon atoms;

$R_3$ is an alkylene group having a length of n+2 carbon atoms;

$R_4$ is an alkylene group having a length of n−2 carbon atoms;

x, y, and z are, independently, integers from 0 to about 100 and n is at least 6;

said mixture being further characterized in that:
- a) the groups depicted within brackets in formula (III) are disposed within the individual molecules such that substantially all molecules of formula (III) in which the sum of x, y and z is 3 or more contain at least two different groups depicted within brackets in formula (III); and
- b) said fluid mixture of hydrocarbons has a pour point of −10° C. or below, a NOACK volatility of 9 or below, and a viscosity index of 150 or above.

22. A fluid mixture in accordance with claim 21 wherein the sum of x, y and z in substantially all molecules of formula (III) is no higher than about 100.

23. A fluid mixture in accordance with claim 21 wherein the sum of x, y and z in substantially all molecules of formula (III) is no higher than about 10.

24. A fluid mixture in accordance with claim 21 wherein the sum of x, y and z in substantially all molecules of formula (III) is no higher than about 6.

25. A fluid mixture in accordance with claim 21 wherein $R_2$ is an unsubstituted polymethylene group having n carbon atoms; $R_3$ is an unsubstituted polymethylene group having n+2 carbon atoms; and $R_4$ is an unsubstituted polymethylene group having n−2 carbon atoms.

26. A fluid mixture in accordance with claim 25 wherein n is 6.

27. A fluid mixture in accordance with claim 25 wherein n is 8.

28. A fluid mixture in accordance with claim 25 wherein n is 6 and wherein the sum of x, y and z in substantially all molecules of formula (I) is no higher than about 10.

29. A fluid mixture in accordance with claim 25 wherein n is 8 and wherein the sum of x, y and z in substantially all molecules of formula (I) is no higher than about 10.

30. A fluid mixture in accordance with claim 21 wherein said mixture has a number average molecular weight of up to about 3,000.

31. A fluid mixture of hydrocarbons having linear backbones and methyl group(s) depending therefrom, said mixture consisting essentially of hydrocarbons having the formula:

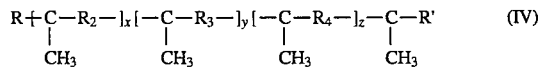

wherein

R and R' are alkyl groups having, independently, 12 to about 40 carbon atoms;

$R_2$ is an alkylene group having a length of n carbon atoms;

$R_3$ is an alkylene group having a length of n+2 carbon atoms;

$R_4$ is an alkylene group having a length of n−2 carbon atoms;

x, y, and z are, independently, integers from 0 to about 100 and n is at least 6;

said mixture being further characterized in that:
- a) the groups depicted within brackets in formula (IV) are disposed within the individual molecules such that substantially all molecules of formula (IV) in which the sum of x, y and z is 3 or more contain at least two different groups depicted within brackets in formula (IV); and
- b) said fluid mixture of hydrocarbons has a pour point of −10° C. or below, and a viscosity index of 150 or above.

32. A fluid mixture in accordance with claim 31 wherein the sum of x, y and z in substantially all molecules of formula (III) is no higher than about 100.

33. A fluid mixture in accordance with claim 31 wherein the sum of x, y and z in substantially all molecules of formula (III) is no higher than about 10.

34. A fluid mixture in accordance with claim 31 wherein the sum of x, y and z in substantially all molecules of formula (III) is no higher than about 6.

35. A fluid mixture in accordance with claim 31 wherein $R_2$ is an unsubstituted polymethylene group having n carbon atoms; $R_3$ is an unsubstituted polymethylene group having n+2 carbon atoms; and $R_4$ is an unsubstituted polymethylene group having n-2 carbon atoms.

36. A fluid mixture in accordance with claim 35 wherein n is 6.

37. A fluid mixture in accordance with claim 35 wherein n is 8.

38. A fluid mixture in accordance with claim 35 wherein n is 6 and wherein the sum of x, y and z in substantially all molecules of formula (I) is no higher than about 10.

39. A fluid mixture in accordance with claim 35 wherein n is 8 and wherein the sum of x, y and z in substantially all molecules of formula (I) is no higher than about 10.

40. A fluid mixture in accordance with claim 31 wherein said mixture has a number average molecular weight of up to about 3,000.

41. A fluid mixture in accordance with claim 1 still further characterized in that said mixture of hydrocarbons contains olefinically unsaturated hydrocarbon molecules in the same molecular weight range as the molecules of formula (I) but wherein the linear backbone itself contains internal olefinic unsaturation, and wherein for each such internal double bond there is one less dependant methylidene group in the molecule; and in that the amount of said olefinically unsaturated hydrocarbon molecules in said fluid mixture is up to about 2 mol percent of said mixture.

42. A fluid mixture in accordance with claim 41 wherein the amount of said modified hydrocarbon molecules is no more than about 1 mol percent of said mixture.

43. A fluid mixture in accordance with claim 11 still further characterized in that said mixture of hydrocarbons contains olefinically unsaturated hydrocarbon molecules in the same molecular weight range as the molecules of formula (II) but wherein the linear backbone itself contains internal olefinic unsaturation, and wherein for each such internal double bond there is one less dependant methylidene group in the molecule; and in that the amount of said olefinically unsaturated hydrocarbon molecules in said fluid mixture is up to about 2 mol percent of said mixture.

44. A fluid mixture in accordance with claim 43 wherein the amount of said modified hydrocarbon molecules is no more than about 1 mol percent of said mixture.

45. A fluid mixture in accordance with claim 7 wherein said mixture of hydrocarbon molecules includes 9-methenyl-1,19-eicosadiene; 9,18-dimethenyl-1,29-triacontadiene; 9,20-dimethenyl-1,29-triacontadiene; 11,18-dimethenyl-1,29-triacontadiene; 9,18,27-trimethenyl-1,39-tetracontanadiene; 9,20,27-trimethenyl-1,39-tetracontanadiene; 9,20,29-trimethenyl-1,39-tetracontanadiene; 11,18,27-trimethenyl-1,39-tetracontanadiene; 9,18,27,36-tetramethenyl-1,49-pentacontanadiene; 9,18,27,38-tetramethenyl-1,49-pentacontanadiene; 9,18,29,36-tetramethenyl-1,49-pentacontanadiene; 9,18,29,38-tetramethenyl-1,49-pentacontanadiene; 9,20,27,36-tetramethenyl-1,49-pentacontanadiene; 9,20,27,38-tetramethenyl-1,49-pentacontanadiene; 9,20,29,36-tetramethenyl-1,49-pentacontanadiene; 11,18,27,36-tetramethenyl-1,49-pentacontanadiene; 11,18,29,36-tetramethenyl-1,49-pentacontanadiene; and 11,20,27,36-tetramethenyl-1,49-pentacontanadiene.

46. A fluid mixture in accordance with claim 27 wherein said mixture of hydrocarbon molecules includes 9-methyl-1,19-eicosane; 9,18-dimethyl-1,29-triacontane; 9,20-dimethyl-1,29-triacontane; 11,18-dimethyl-1,29-triacontane; 9,18,27-trimethyl-1,39-tetracontane; 9,20,27-trimethyl-1,39-tetracontane; 9,20,29-trimethyl-1,39-tetracontane; 11,18,27-trimethyl-1,39-tetracontane; 9,18,27,36-tetramethyl-1,49-pentacontane; 9,18,27,38-tetramethyl-1,49-pentacontane; 9,18,29,36-tetramethyl-1,49-pentacontane; 9,18,29,38-tetramethyl-1,49-pentacontane; 9,20,27,36-tetramethyl-1,49-pentacontane; 9,20,27,38-tetramethyl-1,49-pentacontane; 9,20,29,36-tetramethyl-1,49-pentacontane; 11,18,27,36-tetramethyl-1,49-pentacontane; 11,18,29,36-tetramethyl-1,49-pentacontane; and 11,20,27,36-tetramethyl-1,49-pentacontane.

* * * * *